United States Patent [19]

Saito

[11] Patent Number: 4,625,043
[45] Date of Patent: Nov. 25, 1986

[54] ETHYLIDENENORBORNYL DIMETHYLMETHACRYLOXYSILANE

[75] Inventor: Nobuhiro Saito, Ohta, Japan

[73] Assignee: Toshiba Silicone Co., Ltd., Tokyo, Japan

[21] Appl. No.: 834,096

[22] Filed: Feb. 26, 1986

[30] Foreign Application Priority Data

May 31, 1985 [JP] Japan .................................. 60-116473

[51] Int. Cl.$^4$ .......................... C07F 7/08; C07F 7/18
[52] U.S. Cl. .................................................... 556/442
[58] Field of Search ........................................ 556/442

[56] References Cited

U.S. PATENT DOCUMENTS 2,397,287  3/1946  Ostborg .............................. 556/442
4,301,268  11/1981  Kropac ........................... 556/442 X Primary Examiner—Paul F. Shaver
Attorney, Agent, or Firm—Gary L. Loser

[57] ABSTRACT

An ethylidenenorbornyl dimethylmethacryloxysilane represented by the general formula (I):

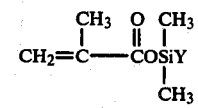

wherein Y represents the formula:

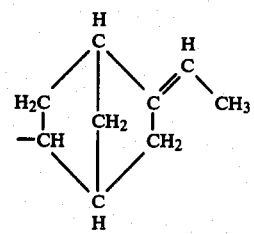

or the formula:

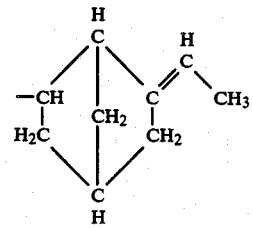

1 Claim, 2 Drawing Figures

ETHYLIDENENORBORNYL DIMETHYLMETHACRYLOXYSILANE

The present application claims priority of Japanese patent application Ser. No. 60-116473 filed May 31, 1985.

BACKGROUND OF THE INVENTION

The present invention relates to an ethylidenenorbornyl dimethylmethacryloxysilane which is a novel compound.

There have been known various kinds of silane compounds wherein a carbon functional group is bonded to a silicon atom through a silicon functional bond. Of such compounds, there may particularly be mentioned trimethylmethacryloxysilane wherein a methacryloxy group is bonded to a silicon (Andreev, D. N., et al., Zhurnal Obshchei Khimii, 30, 2782 (1960)). However, this compound has a disadvantage in stability upon hydrolysis.

There has not been found a silane compound wherein a methacryloxy group is bonded to a silicon atom and which compound also has a reactive double bond in the hydrocarbyl group bonded to the silicon, except for a vinyl compound having high hydrolyzability.

An object of the present invention resides in providing a silane compound having controlled hydrolyzability and also has a reactive double bond in the hydrocarbyl group bonded to the silicon.

SUMMARY OF THE INVENTION

The present invention relates to an ethylidenenorbornyl dimethylmethacryloxysilane represented by the general formula (I):

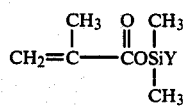

wherein Y represents the formula:

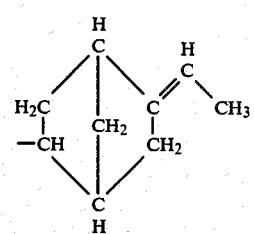

or the formula:

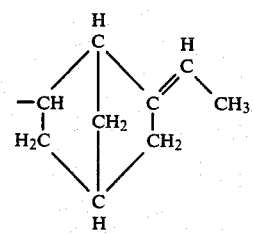

DESCRIPTION OF THE INVENTION

Figure 1:
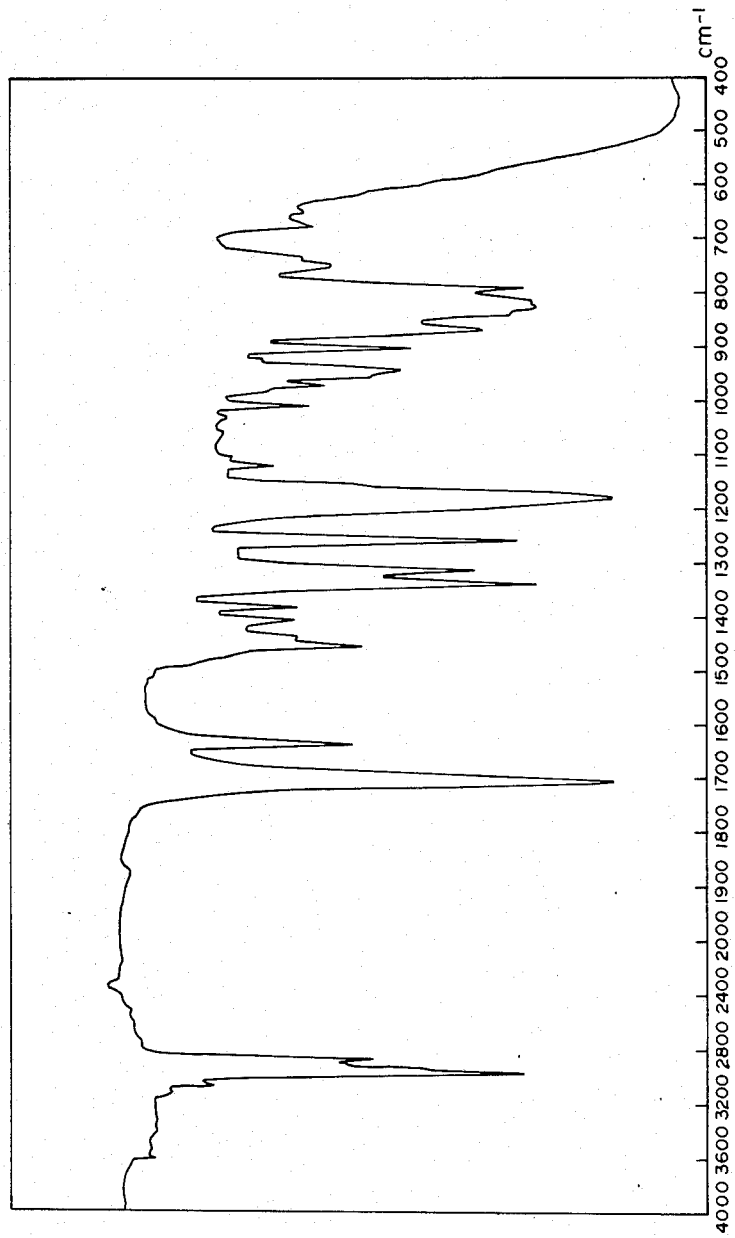
FIGS. 1 and 2 show the IR absorption spectrum and the NMR spectrum, respectively, of the compound obtained in Example 1.
Figure 2:
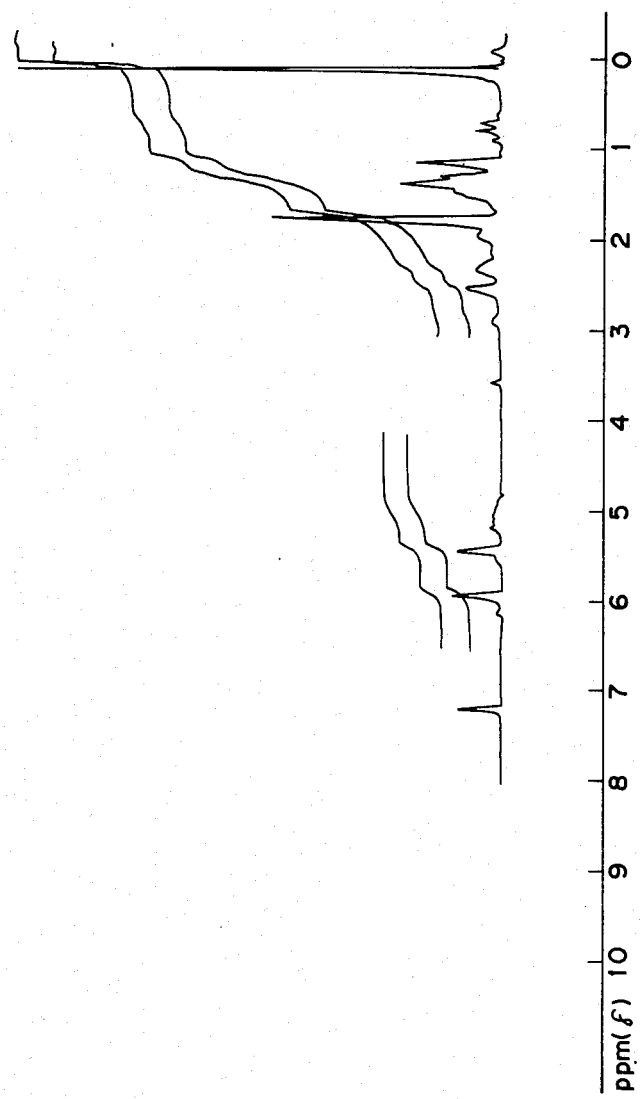

The ethylidenenorbornyl dimethylmethacryloxysilane represented by the general formula (I) of the present invention is a compound wherein a methacryloxy group and an ethylidenenorbornyl group are bonded to a silicon, and which compound can be prepared by reacting methacrylic acid with ethylidenenorbornyl dimethylchlorosilane. The process of preparation of the same is not particularly limited and the reaction is usually conducted in a suitable organic solvent in the presence of an acceptor for hydrogen chloride. One of the preferred methods of preparations is given below.

Methacrylic acid is stirred in a hydrocarbon solvent, an aprotic polar solvent or the like so that the resulting mixture is homogeneous. Next, a suitable acceptor for hydrogen chloride is admixed thereto, followed by heating and stirring. Subsequently, reaction is conducted by adding ethylidenenorbornyl dimethylchlorosilane dissolved in an organic solvent as mentioned above, for example, by dropwise addition etc., followed by further stirring. Such an ethylidenenorbornyl dimethylchlorosilane may be obtained, for example, by hydrosilylation of 5-ethylidenebicyclo(2,2,1)hept-2-ene and dimethylchlorosilane in the presence of a platinum catalyst.

In this instance, two kinds of silanes may be produced simultaneously, since there are two ways for the position of silicon to be added to the double bond in the ring of 5-ethylidenebicyclo(2,2,1)hept-2-ene in the hydrosilylation reaction. This structure may be maintained even after completion of the methacryloxylation reaction.

After completion of the reaction, residual matter may be removed by a suitable method such as filtration etc. Subsequently, the reaction mixture may be purified and dried to give the ethylidenenorbornyl dimethylmethacryloxysilane represented by general formula (I).

As the hydrocarbon solvent to be used in this reaction, there may be mentioned, for example, benzene, toluene, xylene, cyclohexane, n-hexane, etc. As the aprotic polar solvent, there may be mentioned, for example, tetrahydrofuran, dimethylformamide, etc.

It is preferred that the organic solvent be used in an amount such that the amine hydrochloride does not precipitate and interfere with stirring, taking benzene for instance, in an amount equivalent to or more than the silane.

As the acceptor for hydrogen chloride, there may be mentioned triethylamine, pyridine, 1,8-diazabicyclo[5,4,0]undecene-7, etc.

Since this reaction is an exothermic reaction, the rate of dropwise addition may be controlled to hold the reaction temperature from 35° to 60° C., preferably at around 40° C. After a suitable period of dropwise addition for controlling the reaction temperature as mentioned above, further stirring may be continued for at least 10 minutes to complete the reaction.

The compound represented by the general formula (I) of the present invention has a low hydrolysis rate compared with that of trimethylmethacryloxysilane which is a known compound. The present compound has high reactivity since it has two double bonds in the ethylidenenorbornyl group and the methacryloxy group, making it possible to be used as an intermediate for various purposes.

The present invention will be described in more detail by referring to Referential Example and Examples. In the Referential Example and Examples, the term "part(s)" means "part(s) by weight".

EXAMPLES OF THE INVENTION

Referential Example

To a flask equipped with an addition funnel were charged 100 parts of 5-ethylidenebicyclo(2,2,1)hept-2-ene and, as a catalyst, 0.02 part of chloroplatinic acid and the resulting mixture was heated up 30° C. Next, 75 parts of dimethylchlorosilane were added dropwise slowly and the inside of the system was subjected to reflux. The liquid temperature was gradually raised as the reaction progressed. Then the temperature was finally maintained at 80° C. and an additional reaction was conducted for 20 hours.

After removing unreacted matter by means of stripping under reduced pressure (10 mmHg) at 70° C., the reaction mixture was subjected to distillation to obtain 150 parts (yield: 86%) of ethylidenenorbornyl dimethylchlorosilane represented by the following formula:

as a mixture of two compounds, namely (A) and (B): in the Compound (A) Y is represented by the formula:

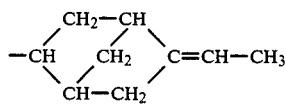

and in the Compound (B) Y is represented by the formula:

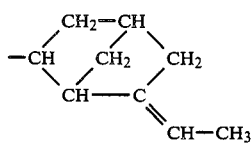

The physical properties of either Compound (A) or (B) are as follows:

| | |
|---|---|
| Boiling point | 97° C./10 mmHg |
| Refractive index ($n_D^{25}$) | 1.491 |
| Specific gravity (25° C.) | 0.992 |
| Molecular weight | 214.5 |
| | (gas mass spectrometry) |

EXAMPLE 1

To a flask equipped with a stirrer, a condenser, a thermometer and a jacket for cooling were charged 55 parts of benzene, 10 parts of methacrylic acid and 0.02 part of hydroquinone and the resulting mixture was stirred until it was homogeneous. To the mixture were added 11 parts of triethylamine and, while maintaining the temperature at 50° C. and stirring, 24 parts of the ethylidenenorbornyl dimethylchlorosilane synthesized in the above Referential Example were added dropwise over 15 minutes, further followed by stirring for 30 minutes to complete the reaction. After completion of the reaction, triethylamine hydrochloride was removed by filtration and the resulting benzene solution containing the reaction product was subjected to distillation to obtain 26 parts of fraction with a boiling point of 126° to 129° C./7 mmHg. The values of physical properties, results of elementary analysis, characteristic absorption and identification thereof of the thus obtained fraction are as shown in Table 1, and it was confirmed that the fraction was ethylidenenorbornyl dimethylmethacryloxysilane. Yield thereof was 89% relative to the theoretical value.

TABLE 1

| Item | Measured value |
|---|---|
| Molecular weight (gas mass spectrometry) | 265 |
| Refractive index ($n_D^{25}$) | 1.4833 |
| Elementary analysis % (values in the brackets show theoretical values) | |
| C | 68.51 (68.39) |
| H | 8.79 (8.80) |
| Si | 10.62 (10.66) |
| IR, characteristic absorption cm$^{-1}$ (values in the brackets show identification) | 1700 (C=O) |
| | 1260 (Si—CH$_3$) |
| | 1170 (C—O—Si with =O) |
| NMR, δ ppm | 0.05 (s, 6H) |
| | 0.9–2.8 (m, 15H) |
| | 4.75–5.25 (m, 1H) |
| | 5.40 (s, 1H) |
| | 5.90 (s, 1H) |

EXAMPLE 2

Each of the samples of ethylidenenorbornyl dimethylmethacryloxysilane obtained in Example 1 and trimethylacryloxysilane as a Comparative Example was tested for hydrolyzability. Namely, 0.05 mole % solutions in carbon tetrachloride of the respective samples of Example 1 and Comparative Example were prepared. To each 50 ml solution thereof were added 50 ml of sodium hydroxide adjusted to pH 8.0, followed by vigorous stirring at room temperature for 15 seconds and the resulting solution was left to stand. After 5 minutes, samples were taken out of the layers of carbon tetrachloride and the absorption intensity of the ester bond at 1170 cm$^{-1}$ was measured by means of IR spectrum analysis using KBr cells to compare with the absorption in the initial carbon tetrachloride solutions at the same wave number. Further each of said solutions were sealed and left to stand. The same experiment was conducted after 1 day and 30 days. The results are as shown in Table 2.

TABLE 2

| | Disappearance of IR absorption at 1170 cm$^{-1}$ | | |
|---|---|---|---|
| Silane compound | After 5 minutes | After 1 day | After 30 days |
| $CH_2{=}C(CH_3){-}COSiMe_2Y$ (with C=O) | No change | No change | Heavily reduced |

TABLE 2-continued

| Silane compound | Disappearance of IR absorption at 1170 cm$^{-1}$ | | |
| --- | --- | --- | --- |
| | After 5 minutes | After 1 day | After 30 days |
| CH$_2$=C(CH$_3$)—C(O)OSiMe$_3$ (Comparative Example) | Disappeared | Disappeared | Disappeared |

Note
Me: Methyl group
Y: As defined above

I claim:

1. An ethylidenenorbornyl dimethylmethacryloxysilane represented by the general formula (I):

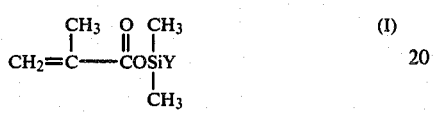

wherein Y represents the formula:

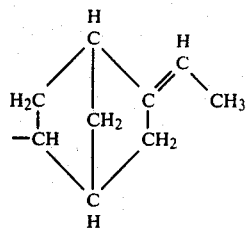

or the formula:

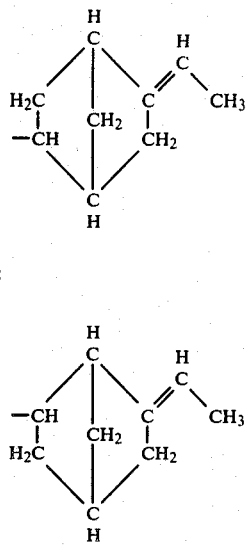

* * * * *